(12) United States Patent
Hayashi et al.

(10) Patent No.: US 7,088,762 B2
(45) Date of Patent: Aug. 8, 2006

(54) MULTI-WAVELENGTH LASER APPARATUS WITH ROTATABLE MIRROR

(75) Inventors: Kenichi Hayashi, Gamagori (JP); Yasutoshi Takada, Kawasaki (JP)

(73) Assignee: Nidek Co., Ltd., Gamagori (JP)

( * ) Notice: Subject to any disclaimer, the term of this patent is extended or adjusted under 35 U.S.C. 154(b) by 201 days.

(21) Appl. No.: 10/670,401

(22) Filed: Sep. 26, 2003

(65) Prior Publication Data
US 2004/0068254 A1    Apr. 8, 2004

(30) Foreign Application Priority Data
Sep. 30, 2002   (JP)   ............................. 2002-287902

(51) Int. Cl.
H01S 3/10      (2006.01)
H01S 3/81      (2006.01)
H01S 3/08      (2006.01)
A61B 18/18     (2006.01)

(52) U.S. Cl. .......................... 372/107; 372/23; 372/93; 372/22

(58) Field of Classification Search ................ 372/107, 372/22, 23, 93
See application file for complete search history.

(56) References Cited
U.S. PATENT DOCUMENTS

| 4,425,648 A | 1/1984 | Holly |
| 5,144,630 A | 9/1992 | Lin |
| 5,249,192 A | 9/1993 | Kuizenga et al. |
| 5,345,457 A | 9/1994 | Zenzie et al. |
| 5,528,612 A | 6/1996 | Scheps et al. |
| 5,764,662 A * | 6/1998 | Pinto ............................ 372/20 |
| 6,636,537 B1 * | 10/2003 | Takada ......................... 372/23 |
| 2002/0027932 A1 | 3/2002 | Takada |

FOREIGN PATENT DOCUMENTS

| EP | 0 526 006 A2 | 2/1993 |
| JP | A 10-65238 | 3/1998 |

* cited by examiner

Primary Examiner—Minsun Harvey
Assistant Examiner—Marcia A. Golub
(74) Attorney, Agent, or Firm—Oliff & Berridge, PLC

(57) ABSTRACT

In a laser apparatus, a rotatable reflection mirror rotatable on or parallel to a resonance optical axis of a laser medium is disposed changeably between a first and second positions by driving of a rotating unit. A first resonance optical system includes a first and second resonant mirrors placed so that the laser medium and the rotatable reflection mirror disposed in the first position are interposed therebetween to resonate light of a first peak wavelength among the peak wavelengths emitted from the laser medium, the first peak wavelength light being to be reflected by the rotatable reflection mirror in the first position between the laser medium and the second resonant mirror, and a first wavelength converting element located between the rotatable reflection mirror disposed in the first position and the second resonant mirror to oscillate second harmonic light of the first peak wavelength light as a first laser beam.

9 Claims, 5 Drawing Sheets

MULTI-WAVELENGTH LASER APPARATUS WITH ROTATABLE MIRROR

BACKGROUND OF THE INVENTION

1. Field of the Invention

The present invention relates to a laser apparatus capable of emitting laser beams of a plurality of different wavelengths.

2. Description of Related Art

As a laser apparatus capable of emitting laser beams of a plurality of different wavelengths, there have been known apparatuses using an argon dye laser capable of changing wavelengths of laser beams to be emitted, a krypton laser capable of emitting laser beams of multiple wavelengths, or others. Those lasers have been used in various fields including a medical field; for example, in ophthalmic surgical operations using laser beams of different wavelengths according to affected parts or treatment purposes.

The aforementioned laser apparatus capable of changing wavelengths of laser beams is concretely an apparatus using a gas laser or a dye laser. These lasers have many problems in a short life of a laser tube, a need for a large amount of electric power, an increased size of the apparatus, etc. Instead thereof, therefore, a laser apparatus capable of emitting (oscillating) laser beams of multiple wavelengths with the use of a solid-state laser has been studied. As the multi-wavelength laser apparatus using the solid-state laser, there has been proposed a laser apparatus constructed such that a mirror disposed in a resonator is moved with respect to a resonance optical path to change a part of the optical path, whereby selectively emitting laser beams of a plurality of different wavelengths. Such apparatus would be requested to prevent variations in laser output relative to wavelength differences.

SUMMARY OF THE INVENTION

The present invention has been made in view of the above circumstances and has an object to overcome the above problems and to provide a laser apparatus which is compact and capable of efficiently emitting laser beams of a plurality of different wavelengths.

Additional objects and advantages of the invention will be set forth in part in the description which follows and in part will be obvious from the description, or may be learned by practice of the invention. The objects and advantages of the invention may be realized and attained by means of the instrumentalities and combinations particularly pointed out in the appended claims.

To achieve the purpose of the invention, there is provided a laser apparatus capable of emitting laser beams of a plurality of different wavelengths, the apparatus including: an exciting light source; a solid-state laser medium which emits light of a plurality of peak wavelengths by light from the exciting light source; a rotatable reflection mirror being rotatable on a resonance optical axis of the laser medium or an axis parallel to the resonance optical axis and being disposed changeably between a first position and a second position; a rotating unit which rotates the rotatable reflection mirror; a first resonance optical system including: a first resonant mirror and a second resonant mirror placed so that the laser medium and the rotatable reflection mirror disposed in the first position are interposed between the first and second resonant mirrors to resonate light of a first peak wavelength among the plurality of peak wavelengths emitted from the laser medium, the first position being a position in which the first peak wavelength light is reflected by the rotatable reflection mirror between the laser medium and the second resonant mirror; and a first wavelength converting element located between the rotatable reflection mirror disposed in the first position and the second resonant mirror to oscillate second harmonic light of the first peak wavelength light as a first laser beam; and a second resonance optical system including: the first resonant mirror and a third resonant mirror placed so that the laser medium and the rotatable reflection mirror disposed in the second position are interposed between the first and third resonant mirrors to resonate light of a second peak wavelength among the plurality of peak wavelengths emitted from the laser medium, the second position being a position in which the second peak wavelength light is reflected by the rotatable reflection mirror between the laser medium and the third resonant mirror, the second peak wavelength being different in wavelength from the first peak wavelength; and a second wavelength converting element located between the rotatable reflection mirror disposed in the second position and the third resonant mirror to oscillate second harmonic light of the second peak wavelength light as a second laser beam.

According to another aspect, the invention provides a laser apparatus capable of emitting laser beams of a plurality of different wavelengths, the apparatus including: an exciting light source; a solid-state laser medium which emits light of a plurality of peak wavelengths by light from the exciting light source; a rotatable output mirror being rotatable on a resonance optical axis of the laser medium or an axis parallel to the resonance optical axis and being disposed changeably between a first position and a second position; a rotating unit which rotates the rotatable output mirror; a first resonance optical system including: a first resonant mirror and a second resonant mirror placed so that the laser medium and the rotatable output mirror disposed in the first position are interposed between the first and second resonant mirrors to resonate light of a first peak wavelength among the plurality of peak wavelengths emitted from the laser medium, the first position being a position in which the first peak wavelength light being reflected by the rotatable output mirror between the laser medium and the second resonant mirror; and a first wavelength converting element located between the rotatable output mirror disposed in the first position and the second resonant mirror to oscillate second harmonic light of the first peak wavelength light as a first laser beam; and a second resonance optical system including: the first resonant mirror and a third resonant mirror placed so that the laser medium and the rotatable output mirror disposed in the second position are interposed between the first and third resonant mirrors to resonate light of a second peak wavelength among the plurality of peak wavelengths emitted from the laser medium, the second position being a position in which the second peak wavelength light is reflected by the rotatable output mirror between the laser medium and the third resonant mirror, the second peak wavelength being different in wavelength from the first peak wavelength; and a second wavelength converting element located between the rotatable output mirror disposed in the second position and the third resonant mirror to oscillate second harmonic light of the second peak wavelength light as a second laser beam, wherein the rotatable output mirror has a property of reflecting the first peak wavelength light and the second peak wavelength light while transmitting the first laser beam and the second laser beam.

BRIEF DESCRIPTION OF THE DRAWINGS

The accompanying drawings, which are incorporated in and constitute a part of this specification illustrate an embodiment of the invention and, together with the description, serve to explain the objects, advantages and principles of the invention.

In the drawings.

DETAILED DESCRIPTION OF THE PREFERRED EMBODIMENTS

Figure 1:
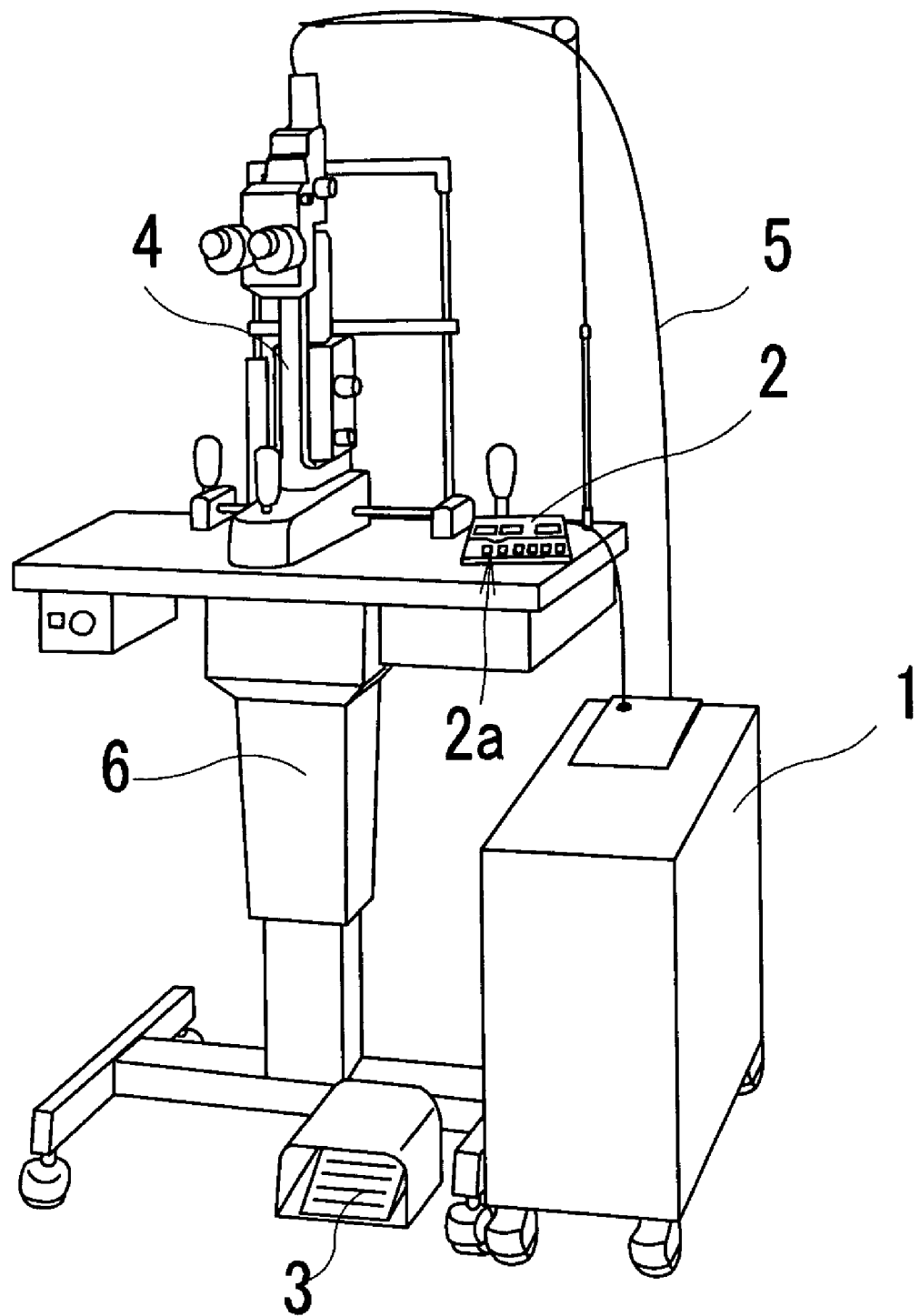
FIG. 1 is a schematic perspective view of an ophthalmic laser photocoagulation apparatus in an embodiment of the present invention.
Figure 2:
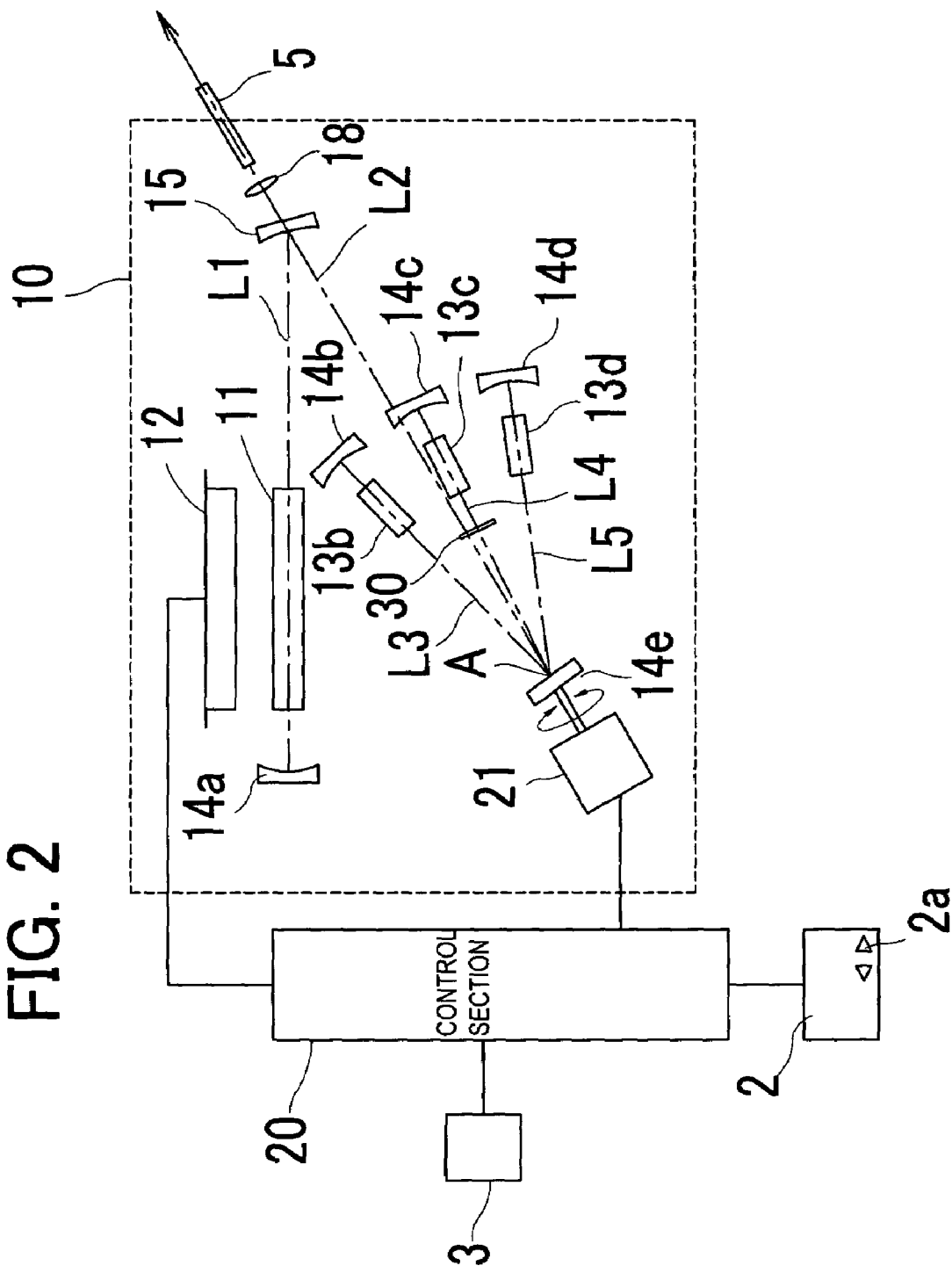
FIG. 2 is a schematic structural view of an optical system and a control system in the apparatus.

A detailed description of a preferred embodiment of a laser apparatus embodying the present invention will now be given referring to the accompanying drawings. FIG. 1 is a schematic perspective view of an ophthalmic laser photocoagulation apparatus using a slit lamp. FIG. 2 is a schematic diagram of an optical system and a control system in the apparatus.

Numeral 1 is an apparatus main unit which houses a laser oscillator 10, a part of a light delivery optical system for delivering a laser beam from the laser oscillator 10 to an affected part of a patient's eye to irradiate the affected part, a control section 20, and others. Numeral 2 is a control board of the apparatus, which is provided thereon with a wavelength selection switch 2a to be used for selecting a wavelength of a laser beam and other various switches for setting laser irradiation conditions. Numeral 3 is a footswitch for generating a trigger signal to start laser irradiation.

Numeral 4 is a slit lamp containing an observation optical system for allowing an operator to observe the patient's eye and a part of the light delivery optical system. Numeral 5 is an optical fiber through which the laser beam is delivered from the main unit 1 to the slit lamp 4. Numeral 6 is a stand which mounts thereon the slit lamp 4 movably in a vertical direction.

Numeral 10 is a laser oscillator internally provided with an Nd:YAG crystal 11 (hereinafter, referred to as a "rod") which is a solid-state laser medium, a laser diode 12 (hereinafter, referred to as an "LD") serving as an exciting light source, nonlinear crystals 13b, 13c, and 13d (hereinafter, referred to as an "NLC") serving as wavelength converters (wavelength converting elements), total reflection mirrors (high reflectors) 14a to 14e (hereinafter, referred to as an "HR") serving as resonant mirrors, and an output mirror 15. It is to be noted that the nonlinear crystals may be selected from among KTP crystal, LBO crystal, BBO crystal, or the like. In the present embodiment, the KTP crystal is used.

The Nd:YAG crystal emits light having a plurality of oscillation lines (peak wavelengths) in the near-infrared region by an exciting light from the exciting light source. Therefore, the apparatus in the present embodiment is constructed such that each second harmonic light of three oscillation lines; about 1064 nm, about 1123 nm, about 1319 nm, which are the wavelengths with high power among the plural oscillation lines emitted from the above crystal, is generated with the use of the nonlinear crystal, thereby emitting (oscillating) the visible laser beams of three colors with wavelengths of about 532 nm (green), about 561 nm (yellow), and about 659 nm (red), respectively.

On the optical path having an optical axis L1 on which the rod 11 is placed, an HR 14a is disposed at one end of the optical path and the output mirror 15 is arranged at a predetermined inclination angle with the optical path at the other end thereof. The HR 14a in the present embodiment has the property of totally reflecting the light of about 1064 nm to about 1319 nm. Besides the HR 14a, another reflector may be used if only it can widely reflect the light of wavelengths in the near-infrared region including about 1064 nm, about 1123 nm, and about 1319 nm. The output mirror 15 has the property of totally reflecting the light of about 1064 nm to about 1319 nm, while transmitting the light of about 532 nm to about 659 nm. The laser beam having passed through the output mirror 15 is concentrated by a condensing lens 18 and delivered from the main unit 1 to the slit lamp 4 through the fiber 5.

Figure 3:
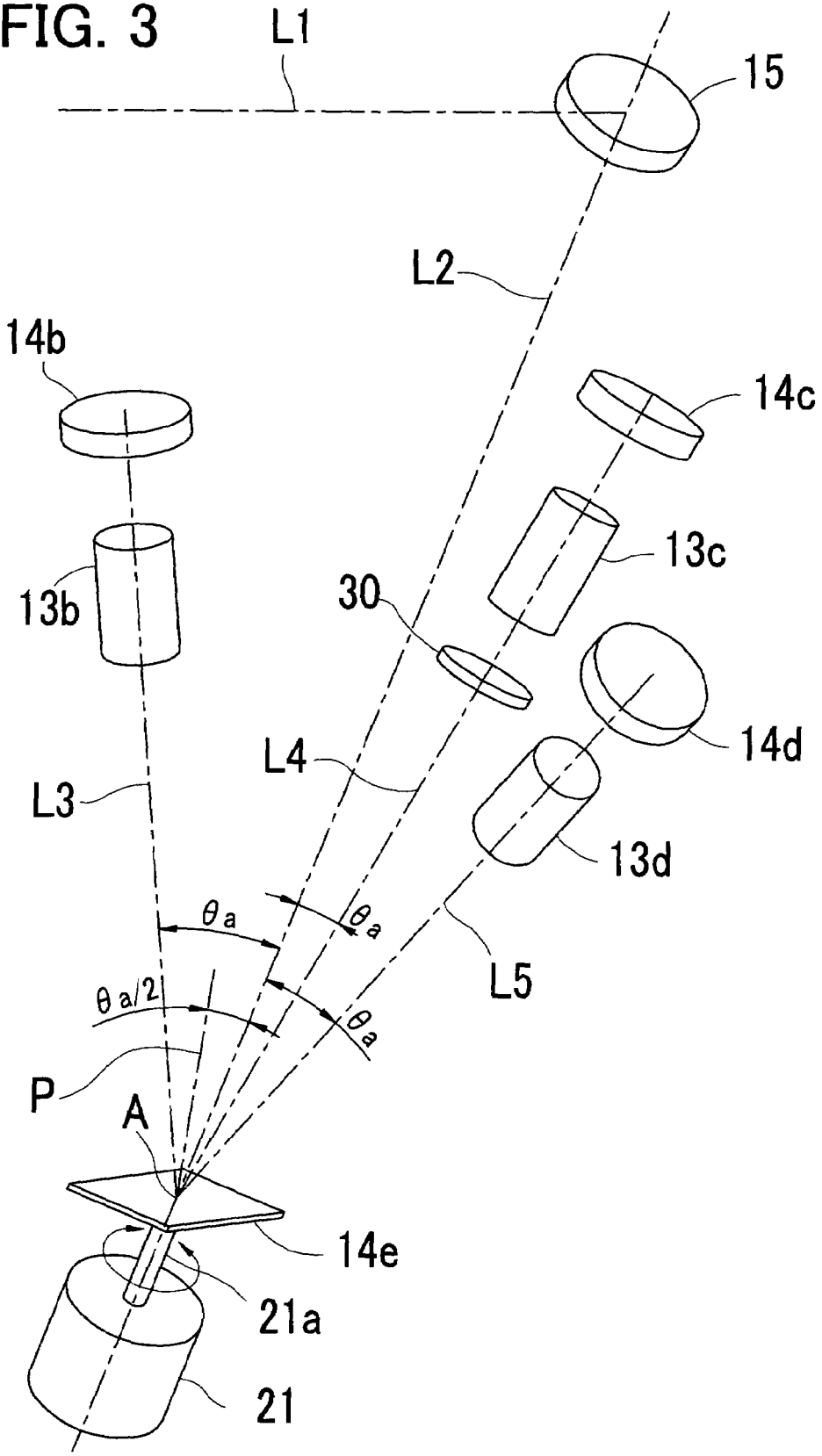
FIG. 3 is a schematic arrangement view of a resonance optical system.

The HR 14e is placed at one end of an optical path having an optical axis L2 (i.e. an axis of light incident on the output mirror 15) to be provided by reflection of the optical axis L1 by the output mirror 15 (disposed at the other end of the optical path). This HR 14e has the property of totally reflecting the light of about 1064 nm to about 1319 nm and the light of about 532 nm to about 659 nm. The HR 14e is rotated on the optical axis L2 by a pulse motor 21. As shown in FIG. 3, the optical axis L2 is coaxial with the center axis of a rotating shaft 21a of the motor 21. The HR 14e is fixed to the rotating shaft 21a so that a perpendicular line P to a reflection surface of the HR 14e is inclined at an angle θa/2 with respect to the optical axis L2. That is, the angle θa/2 is the angle of incidence on the HR 14e. According to the rotation (a rotating angle or position) of the HR 14e, the optical axis L2 is reflected at a constant angle θa to coincide with the optical axes L3, L4, and L5 respectively. Specifically, the optical axes L3, L4, and L5 are set so as to intersect with one another at one point A on the optical axis L2. The reflection surface of the HR 14e is positioned at the intersecting point A. When the HR 14e is rotated by driving of the motor 21 and placed in one of first, second, and third positions, the optical path having the optical axis L5, L4, or L3, setting the reflecting direction of the HR 14e, forms a dedicated resonance optical path of light having a corresponding one of different wavelengths.

It is to be noted that the optical axis L2 and the center axis of the rotating shaft 21a of the motor 21 are made coaxial in the present embodiment, but they may be made parallel. In this parallel case, similarly, the optical axis L2 is reflected at the constant angle θa to coincide with the optical axes L3, L4, and L5 respectively according to the rotation (a rotating angle or position) of the HR 14e.

The HR 14d is placed at one end of the optical path having the optical axis L5 (the HR 14e is placed at the other end of the same). The NLC 13d is interposed between the HR 14d and the HR 14e. The NLC 13d is placed so as to generate the light of about 659 nm which is the second harmonic light from the light of about 1319 nm. The HR 14d has the property of totally reflecting the light of about 1319 nm and the light of about 659 nm. In other words, the HR 14d used for oscillating the laser beam of about 659 nm has only to have the property of totally reflecting at least the light of about 659 nm and the light of about 1319 nm.

This optical system having the optical axes L1, L2, and L5 constructs a first resonance optical system including a resonator configuration in which the HR 14a and the HR 14d are arranged in a pair so that the rod 11 is interposed between them. Thus, the light of about 659 nm generated by the NLC 13d can be emitted through the output mirror 15 without being blocked by the rod 11.

The HR 14c is placed at one end of the optical path having the optical axis L4 (and the HR 14e is placed at the other end of the same). The NLC 13c is interposed between the HR 14c and the HR 14e. The NLC 13c is disposed so as to generate the light of about 561 nm which is the second harmonic light from the light of about 1123 nm. The HR 14c has the property of totally reflecting the light of about 1123 nm and the light of about 561 nm. More specifically, the HR 14c used for oscillating the laser beam of about 561 nm has only to have the property of totally reflecting at least the light of about 561 nm and the light of about 1123 nm. In the present embodiment, the reflection property of the HR 14c for oscillating the laser beam of about 659 nm is desired to include the reflection rate of 50% or less with respect to the light of the oscillation lines with short-wavelengths of about 1115.9 nm or less which provide a higher gain than about 1123 nm among the oscillation lines emitted from the Nd:YAG crystal, and the reflection rate of 20% or less with respect to the light of about 1064 nm. It is to be noted that the light of about 1115.9 nm among the oscillation lines from the Nd:YAG crystal is close in wavelength to the light of about 1123 nm. It therefore may be difficult to provide the reflection property of the HR 14c with a difference in reflection rate between those close wavelengths. In this case, a wavelength selectable element 30 such as an etalon is disposed between the NLC 13c and the HR 14e so that the light of about 1123 nm is selectively taken out.

This optical system having the optical axes L1, L2, and L4 constructs a second resonance optical system including a resonator configuration in which the HR 14a and the HR 14c are arranged in a pair so that the rod 11 is interposed between them. Thus, the light of about 561 nm generated by the NLC 13c can be emitted through the output mirror 15.

The HR 14b is placed at one end of the optical path having the optical axis L3 (and the HR 14e is placed at the other end of the same). The NLC 13b is interposed between the HR 14b and the HR 14e. The NLC 13b is disposed so as to generate the light of about 532 nm which is the second harmonic light from the light of about 1064 nm. The HR 14b has the property of totally reflecting the light of about 1064 nm and the light of about 532 nm. To be more specific, the HR 14b for oscillating the laser beam of about 532 nm has only to have the property of totally reflecting at least the light of about 532 nm and the light of about 1064 nm.

This optical system having the optical axes L1, L2, and L3 constructs a third resonance optical system including a resonator configuration in which the HR 14a and the HR 14b are arranged in a pair so that the rod 11 is interposed between them. Thus, the light of about 561 nm generated by the NLC 13c can be emitted through the output mirror 15.

To construct the above resonance optical systems to emit the laser beams of corresponding wavelengths, the rotating positions of the HR 14e are controlled as follows. When power is applied to the laser apparatus, at first, the control section 20 drives the motor 21 to return the HR 14e to a predetermined angle position (an initial position). Successively, using this position as a reference angle position, the control section 20 causes the HR 14e to rotate to an angle position (a first, second, or third position) determined to emit the laser beam of a selected wavelength. Specifically, the first resonance optical system is constructed when the HR 14e is rotated to change the orientation of the reflection surface so that the reflection direction of the optical axis L2 becomes coincide with the optical axis L5, (i.e., when the HR 14e is rotated to the first position), thereby emitting the laser beam of about 659 nm. Alternatively, the second resonance optical system is constructed when the HR 14e is rotated so that reflection direction of the optical axis L2 becomes coincide with the optical axis L4 (i.e., when the HR 14e is rotated to the second position), thereby emitting the laser beam of about 561 nm. Further, the third resonance optical system is constructed when the HR 14e is rotated so that reflection direction of the optical axis L2 becomes coincide with the optical axis L3 (i.e., when the HR 14e is rotated to the third position), thereby emitting the laser beam of about 532 nm. It is to be noted that a limit sensor not shown or the like is used to detect the angle position of the HR 14e for adjustment of the HR 14e to the predetermined angle position (the reference angle position).

Next, explanation is made on methods of emitting laser beams of a plurality of different wavelengths by means of the above structures.

A Method of Emitting a Laser Beam of 659 nm

An operator operates the switch 2a to select "red" (659 nm) as the color (wavelength) of a laser beam to be used in a surgical operation. When the red is selected, the control section 20 drives the motor 21 to rotate the HR 14e, switching over the optical paths so as to reflect the optical axis L2 to the optical axis L5.

The control section 20, upon receipt of a trigger signal from the footswitch 3, applies electric current to the LD 12 to thereby excite the rod 11. It is to be noted that both end faces of an Nd:YAG crystal used as the rod 11 are applied in advance with an AR (anti reflective) coating for enhancing transmittance with respect to each of the light beams of about 1064 nm, about 1123 nm, and about 1319 nm.

When the rod 11 is excited, the light of about 1319 nm is resonated between the HRs 14a and 14d and converted to the second harmonic light thereof; the light of about 659 nm by the NLC 13d disposed on the optical axis L5. The thus produced laser beam of about 659 nm is allowed to pass through the output mirror 15 and concentrated by the condensing lens 18 into the fiber 5. Then, the laser beam is irradiated from an irradiation port of the slit lamp 4 toward the patient's eye.

A Method of Emitting a Laser Beam of 561 nm

An operator operates the switch 2a to select "yellow" (561 nm) as the color (wavelength) of a laser beam to be used in a surgical operation. When the yellow is selected, the control section 20 drives the motor 21 to rotate the HR 14e to switch the optical paths so as to reflect the optical axis L2 to the optical axis L4. The control section 20 then applies electric current to the LD 12 in response to a trigger signal from the footswitch 3, thereby exciting the rod 11.

When the rod 11 is excited, the light of about 1123 nm is resonated between the HRs 14a and 14c and converted to the second harmonic light thereof; the light of about 561 nm by the NLC 13c disposed on the optical axis L4. The thus produced laser beam of about 561 nm is allowed to pass through the output mirror 15 and enter the fiber 5. Then, the laser beam is irradiated from the irradiation port of the slit lamp 4 toward the patient's eye.

A Method of Emitting a Laser Beam of 532 nm

An operator operates the switch 2a to select "green" (532 nm) as the color (wavelength) of a laser beam to be used in a surgical operation. When the green is selected, the control section 20 drives the motor 21 to rotate the HR 14e to switch the optical paths so as to reflect the optical axis L2 to the optical axis L3. Upon receipt of a trigger signal from the footswitch 3, the control section 20 applies electric current to the LD 12 to thereby excite the rod 11.

When the rod 11 is excited, the light of about 1064 nm is resonated between the HRs 14a and 14b and converted to the second harmonic light thereof; the light of about 532 nm by the NLC 13b disposed on the optical axis L3. The thus produced laser beam of about 532 nm is allowed to pass through the output mirror 15 and enter the fiber 5. Then, the laser beam is irradiated from the irradiation port of the slit lamp 4 toward the patient's eye.

With the above structures, the single total reflection mirror 14e has only to be rotated in order to switch the optical paths. This makes it possible to maintain the incident angle of the light incident upon the total reflection mirror 14e and efficiently emit the laser beams of three different wavelengths respectively without a reduction in power. Since the optical axes L3, L4, and L5 are provided at a deflection angle θa with the optical axis L2, that is, in three-dimensional relation around the optical axis L2. This makes it possible to realize compact resonance optical systems and achieve a reduced size of the oscillator 10.

Figure 4:
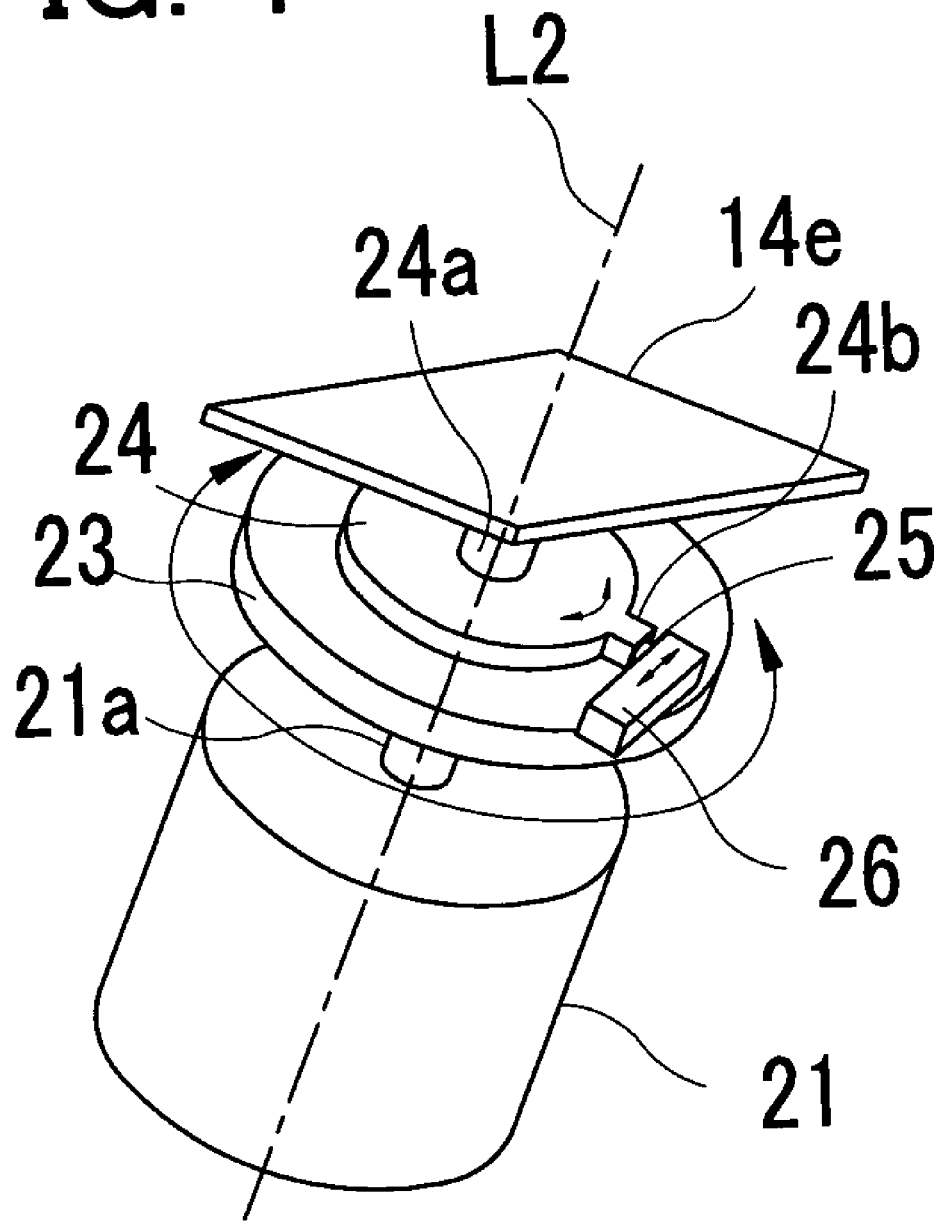
FIG. 4 is a schematic structural view of a structure for rotational fine movement of a total reflection mirror.

To further enhance the emission efficiency of the laser beam, an output sensor is disposed between the output mirror 15 and the condensing lens 18 to detect the output power of the laser beam and, based on a detected result by the output sensor, the angle position of the HR 14e is fine adjusted so that the highest output power of the laser beam is detected. For the fine adjustment of the angle position of the HR 14e, a piezoelectric element 26 may be used as shown in FIG. 4. Specifically, a table 23 is attached to the rotating shaft 21a of the motor 21 and the piezoelectric element 26 is fixed to the table 23. In addition, a rotatable plate 24 is rotatably mounted on the table 23. The HR 14e is fixed to a shaft 24a of the rotatable plate 24 so that the perpendicular line to the reflection surface of the HR 14e is inclined at an angle θa/2 with the optical axis L2 as in the above case. A hook 24b of the rotatable plate 24 is connected with one end of a shaft 25. The other end of the shaft 25 is connected with the piezoelectric element 26. This structure allows expansion and contraction of the piezoelectric element 26 under the control of the control section 20, thereby performing fine adjustment of the angle position of the HR 14e.

Figure 5:
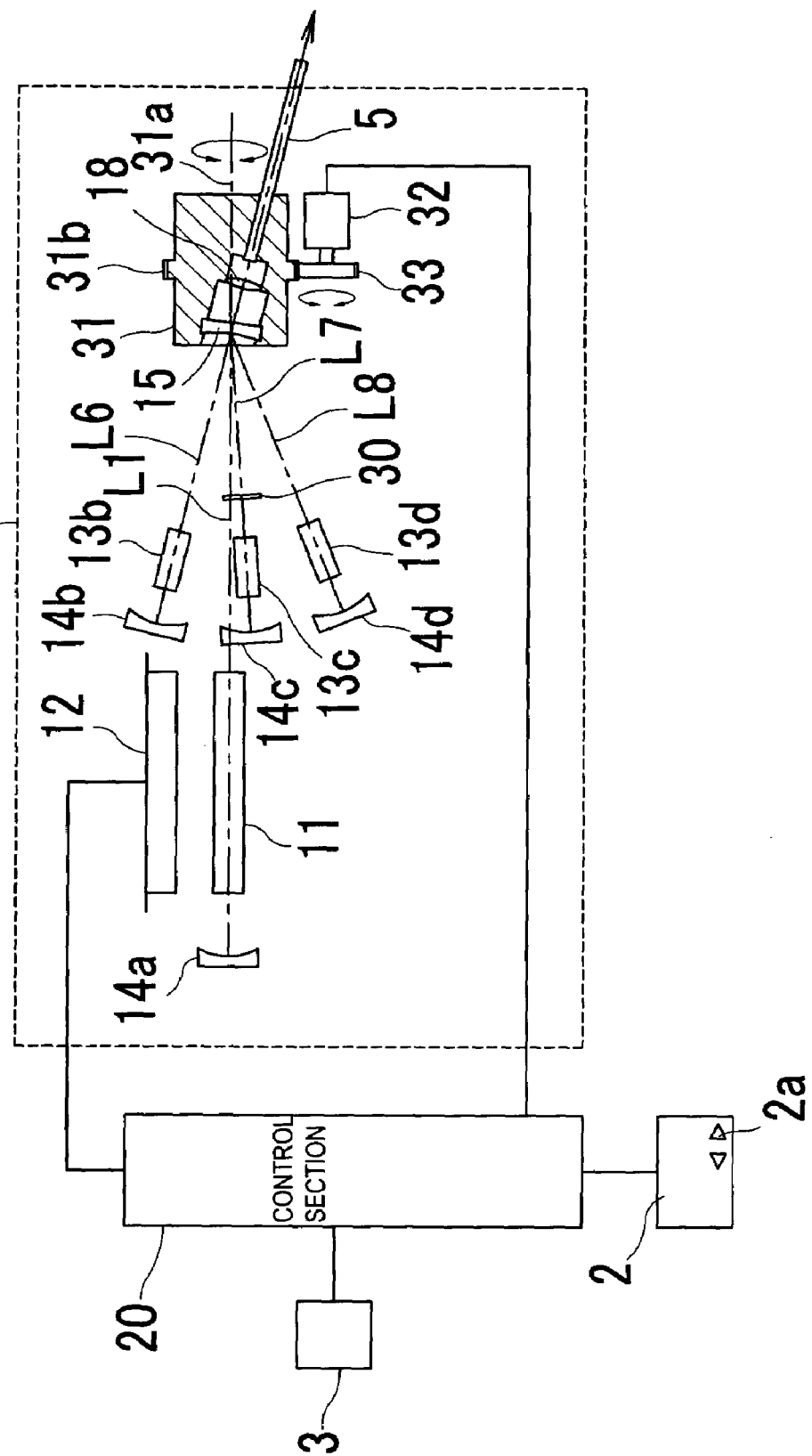
FIG. 5 is a schematic structural view of an optical system and a control system in another embodiment of the present invention.

In the above embodiment, the total reflection mirror HR 14e is rotated to selectively switch the first, second, and third resonance optical systems. Instead of the HR 14e, the output mirror 15 may be rotated as shown in FIG. 5. In this example, the elements indicated by the same numerals as those in the above embodiment have the same functions and their explanations are omitted. The optical axes L3, L4, and L5 correspond to optical axes L6, L7, and L8 respectively. These optical axes L6, L7, and L8 are each provided at an angle θa with the optical axis L1.

The output mirror 15 is fixed to a rotatable holder 31 so that the normal line of the mirror 15 is inclined at an angle θa with the optical axis L1. The rotatable holder 31 is provided with a rotating shaft 31a having a center axis coaxial with the optical axis L1. In the holder 31, in the direction to output a laser beam through the output mirror 15 (i.e. on an optical path on the transmittance side of the output mirror 15), a condensing lens 18 and a fiber 5 are fixedly placed. The holder 31 is also formed with a gear 31b on the periphery. This gear 31b engages with a gear 33 fixed to a pulse motor 32. The motor 32 is driven in response to a command from the control section 20. By rotation of the rotatable holder 31 by the motor 32, the reflecting direction of the output mirror 15 is changed, selectively constructing the first resonance optical system having the optical axes L1 and L8, the second resonance optical system having the axes L1 and L7, and the third resonance optical system having the axes L1 and L6. The condensing lens 18 and the fiber 5 are rotated together with the output mirror 15, so that the laser beam having passed through the output mirror 15 can efficiently be delivered through the condensing lens 18 and the fiber 5. This structure makes it possible to reduce the optical path by a length corresponding to the above mentioned optical axis L2. Thus, as compared with the above embodiment, a more reduced size of the laser oscillator 10 can be realized.

In the above embodiments, the laser apparatus is constructed to emit the laser beams of three different wavelengths. Besides this, the laser apparatus may be constructed to emit laser beams of for example two wavelengths or four wavelengths.

As explained above, according to the present invention, laser beams of a plurality of different wavelengths can be emitted by a compact laser apparatus.

While the presently preferred embodiment of the present invention has been shown and described, it is to be understood that this disclosure is for the purpose of illustration and that various changes and modifications may be made without departing from the scope of the invention as set forth in the appended claims.

What is claimed is:

1. A laser apparatus capable of emitting laser beams of a plurality of different wavelengths, the apparatus including:
   an exciting light source;
   a solid-state laser medium which emits light of a plurality of peak wavelengths by light from the exciting light source;
   a rotatable reflection mirror placed so that a line that is perpendicular to a reflection surface of the rotatable reflection mirror is inclined at a predetermined non-zero angle with respect to a resonance optical axis of the laser medium;
   a rotating unit, having a rotating axis made coaxial with or parallel to the resonance optical axis, which rotates the rotatable reflection mirror about the rotating axis so that the rotatable reflection mirror is disposed changeably between a first position and a second position and the predetermined inclined non-zero angle of the line that is perpendicular to the reflection surface with respect to the resonance optical axis is constant;
   a first resonance optical system including:
      a first resonant mirror and a second resonant mirror placed so that the laser medium and the rotatable reflection mirror disposed in the first position are interposed between the first and second resonant mirrors to resonate light of a first peak wavelength among the plurality of peak wavelengths emitted from the laser medium, the first position being a position in which the first peak wavelength light is reflected by to rotatable reflection mirror between the laser medium and the second resonant mirror; and
      a first wavelength converting element located between the rotatable reflection mirror disposed in the first position and the second resonant mirror to oscillate second harmonic light of the first peak wavelength light as a first laser beam; and a second resonance optical system including:
the first resonant mirror and a third resonant mirror placed so that the laser medium and the rotatable reflection mirror disposed in the second position are interposed between the first and third resonant mirrors to resonate light of a second peak wavelength among the plurality of peak wavelengths emitted from the laser medium, the second position being a position in which the second peak wavelength light is reflected by the rotatable reflection mirror between the laser medium and the third resonant mirror, the second peak wavelength being different in wavelength from the first peak wavelength; and a second wavelength converting element located between the rotatable reflection mirror disposed in the second position and the third resonant mirror to oscillate second harmonic light of the second peak wavelength light as a second laser beam.

2. The laser apparatus according to claim 1, further including an output mirror located on an optical path between the laser medium and the rotatable reflection mirror disposed in the first position or the second position, the output mirror having a property of reflecting the first peak wavelength light and the second peak wavelength light while transmitting the first laser beam and the second laser beam.

3. The laser apparatus according to claim 1, wherein the rotatable reflection mirror is used as an output mirror and has a property of reflecting the first peak wavelength light and the second peak wavelength light while transmitting the first laser beam and the second laser beam.

4. The laser apparatus according to claim 1, wherein the rotatable reflection mirror is placed so that a perpendicular line or a normal line to a reflection surface of the reflection mirror is inclined at a predetermined non-zero angle with the resonance optical axis.

5. The laser apparatus according to claim 1, wherein the apparatus is an ophthalmic laser treatment apparatus,
the first wavelength converting element has a property of converting the first peak wavelength light in a near-infrared region to the first laser beam of a wavelength in a visible region, and
the second wavelength converting element has a property of converting the second peak wavelength light in a near-infrared region to the second laser beam of a wavelength in a visible region.

6. A laser apparatus capable of emitting laser beams of a plurality of different wavelengths, the apparatus including:
an exciting light source;
a solid-state laser medium which emits light of a plurality of peak wavelengths by light from the exciting light source;
a rotatable output mirror being rotatable on a resonance optical axis of the laser medium or an axis parallel to the resonance optical axis and being disposed changeably between a first position and a second position;
a rotating unit which rotates the rotatable output mirror;
a first resonance optical system including:
a first resonant mirror and a second resonant mirror placed so that the laser medium and the rotatable output mirror disposed in the first position are interposed between the first and second resonant mirrors to resonate light of a first peak wavelength among the plurality of peak wavelengths emitted from the laser medium, the first position being a position in which the first peak wavelength light being reflected by the rotatable output mirror between the laser medium and the second resonant mirror; and a first wavelength converting element located between the rotatable output mirror disposed in the first position and the second resonant mirror to oscillate second harmonic light of the first peak wavelength light as a first laser beam; and a second resonance optical system including:
the first resonant mirror and a third resonant mirror placed so that the laser medium and the rotatable output mirror disposed in the second position are interposed between the first and third resonant mirrors to resonate light of a second peak wavelength among the plurality of peak wavelengths emitted from the laser medium, the second position being a position in which the second peak wavelength light is reflected by the rotatable output mirror between the laser medium and the third resonant mirror, the second peak wavelength being different in wavelength from the first peak wavelength; and a second wavelength converting element located between the rotatable output mirror disposed in the second position and the third resonant mirror to oscillate second harmonic light of the second peak wavelength light as a second laser beam, wherein the rotatable output mirror has a property of reflecting the first peak wavelength light and the second peak wavelength light while transmitting the first laser beam and the second laser beam.

7. The laser apparatus according to claim 6, further including:
an optical fiber located on an optical path on a transmittance side of the rotatable output mirror; and
a condensing lens which concentrates the laser beam having passed through the rotatable output mirror into the fiber,
wherein the rotatable unit is arranged to rotate the optical fiber and the condensing lens together with the rotatable output mirror.

8. The laser apparatus according to claim 6, wherein the rotatable output mirror is placed so that a perpendicular line or a normal line to a reflection surface of the output mirror is inclined at a predetermined non-zero angle with the resonance optical axis.

9. The laser apparatus according to claim 6, wherein the apparatus is an ophthalmic laser treatment apparatus,
the first wavelength converting element has a property of converting the first peak wavelength light in a near-infrared region to the first laser beam of a wavelength in a visible region, and
the second wavelength converting element has a property of converting the second peak wavelength light in a near-infrared region to the second laser beam of a wavelength in a visible region.

* * * * *